United States Patent [19]

Berger et al.

[11] Patent Number: 5,024,829
[45] Date of Patent: Jun. 18, 1991

[54] METHOD OF IMAGING CORONARY THROMBI

[75] Inventors: Harvey J. Berger, Devon, Pa.; Jamshid Maddahi; Daniel Berman, both of Beverly Hills, Calif.

[73] Assignee: Centocor, Inc., Malvern, Pa. ; by said Harvey J. Berger

[21] Appl. No.: 274,383

[22] Filed: Nov. 21, 1988

[51] Int. Cl.$^5$ .................... A61K 49/02; A61K 39/395
[52] U.S. Cl. .................................. 424/1.1; 424/85.91
[58] Field of Search ................ 424/1.1, 85.91; 534/14; 530/388, 389

[56] References Cited

U.S. PATENT DOCUMENTS

| | | | |
|---|---|---|---|
| 4,427,646 | 1/1984 | Olexa et al. | 424/1.1 |
| 4,455,290 | 6/1984 | Olexa et al. | 424/1.1 |
| 4,783,330 | 11/1988 | Furie et al. | |
| 4,820,505 | 4/1989 | Ginsberg et al. | 424/1.1 X |

FOREIGN PATENT DOCUMENTS

| | | |
|---|---|---|
| 0249007 | 12/1987 | European Pat. Off. . |
| 88/07382 | 10/1988 | PCT Int'l Appl. . |
| 89/05187 | 11/1989 | PCT Int'l Appl. . |

OTHER PUBLICATIONS

Morris, William; Ed. "American Heritage Dictionary", 1976, Houghton Mifflin Company, pg. 1341.
B. Kudryk et al., "Specificity of a Monoclonal Antibody for the $NH_2$—Terminal Region of Fibrin", *Mol. Immunol.*, 21:89–94 (1984).
L. C. Knight et al., "Evaluation of In-III Labeled Anti--Fibrin Antibody for Imaging Vascular Thombi", (Abs. 402), *J. Nuclear Med.*, 27:975 (1986).
E. K. J. Pawels et al., "Imaging of Thrombi with Tc-99m Labeled Fibrin-Specific Monoclonal Antibody", (Abs. 403), *J. Nuclear Med.*, 27:975 (1986).
R. P. McEver et al., "Identification of Two Structurally and Functionally Distinct Sites . . .", *J. Biol. Chem.*, 258:5269–75 (1983).
R. P. McEver and M. N. Martin, "A Monoclonal Antibody to a Membrane Glycoprotein Binds Only to Activated Platelets", *J. Biol. Chem.*, 259:9799–9804 (1984).
P. E. Stenberg et al., "A Platelet Alpha-Granule Membrane Protein . . .", *J. Cell Biol.*, 101:880–886 (1985).

*Primary Examiner*—John S. Maples
*Attorney, Agent, or Firm*—Hamilton, Brook, Smith & Reynolds

[57] ABSTRACT

A method for instantaneous imaging of coronary thrombi is disclosed. A radiolabeled, thrombus-specific antibody or antibody fragment is administered into a coronary artery and the label is detected to obtain a visual image of the thrombus.

12 Claims, 13 Drawing Sheets

Ex vivo image

In vivo image

A. In vivo image of a 0.4 mg partially occlusive thrombus

B. Ex vivo image of the same 0.4 mg thrombus 15 minutes 4 hours 24 hours

C. Injection of IC STK
B. 12 minutes prior to STK
A. 24 minutes prior to STK
F. 58 minutes post STK
E. 24 minutes post STK
D. 12 minutes after STK
Fig. 13

METHOD OF IMAGING CORONARY THROMBI

DESCRIPTION

Background

Coronary thrombosis plays a major role in clinical instability and development of myocardial infarction in patients with angina. The process of intravascular thrombosis is complex. One of the first events of this process is the activation of platelets with thrombin, resulting in the adherence of these cells to the modified or injured vascular wall. Thrombin itself also serves to assist in the cleavage of fibrinogen to the cross-linked polymer fibrin. This clotting mechanism leads to thrombus formation.

The final common pathway of coronary artery occlusion that leads to acute myocardial infarction is thrombus formation at the site of ulcerated or fissured atheromatous plaque. See, for example, Chandler, A.B. et al., *Am. J. Cardiol.*, 34:823-830 (1974); Penther, P., *Am. Heart J.*, 94:392-400 (1977). Intracoronary application of thrombolytic agents and intravenous application of streptokinase have been used to achieve lysis of intracoronary thrombi. See, e.g., Ganz, W. et al., *Am. Heart J.*, 102:1145-1149 (1981); Ganz et al., *Am. J. Cardio.*, 53:1209-1217 (1984).

Although a clot may be successfully lysed, residual thrombi may be responsible for renewed blockage of the reopened coronary artery. Gash, A.K. et al., *Am. J. Cardiol.*, 57:175-177 (1986): Shaer, D.H. et al., *Circulation*, 76:57-62 (1987). Coronary angioplasty may not even prevent reblockage and in the presence of residual thrombus, angioplasty procedures may precipitate a sudden reocclusion, mandating bypass surgery. Sugrue, D. et al., *Br. Heart J.*, 56:62-66 (1986). In addition, since balloon angioplasty injures the vessel wall and exposes subendothelial cell layers, the procedure may present a stimulus for platelet accumulation, thrombosis and plaque formation.

Development of methods for thrombus imaging have been stimulated by these clinical problems. Platelets were first labeled with the gamma emitter Indium-111 (In-111) more than a decade ago. Thakur, M.L. et al., *Thromb. Res.*, 9:345-357 (1976). Powers et al., *Neurology*, 32:938-943 (1982). This method of imaging intraarterial or venous thrombi has not gained widespread clinical application because of the following disadvantages: 1) visualization of small thrombi is difficult, 2) visualization of coronary thrombi is made difficult by the considerable blood pool "background" activity, 3) In-111 platelet imaging is effective only in fresh thrombi which are actively incorporating platelets, 4) because in vitro blood separation, washing, and labeling is required, platelet labeling is time consuming, expensive, and limited to skilled personnel. Thus, there is little potential of developing a kit for easy application of this method.

A reliable and rapid method for visualization of coronary thrombi is needed to overcome the disadvantages of the labeled platelet technique, not only in clinical applications following thrombolytic therapy, but also in studying the pathology of artery reocclusion.

SUMMARY OF THE INVENTION

This invention pertains to a rapid method of imaging coronary thrombi by the intracoronary arterial administration of radiolabeled monoclonal antibodies specific for a thrombus component such as fibrin. The method comprises the administration of a thrombus-specific imaging agent into a coronary artery of an individual suspected of having a coronary thrombus. The imaging agent comprises a radiolabeled monoclonal antibody or fragment thereof that is specific for a thrombus component. With direct intracoronary arterial administration, the accumulation of label at the site of coronary thrombi will be virtually instantaneous. The signal generated by the label is detected and visualized by a photoscanning device such as a gamma camera and converted into an image of the plaque.

The method and compositions of this invention offer several advantages over previous thrombus imaging techniques. In particular, because the components of thrombus which are targets of the imaging agents (for example, fibrin) are thrombus-specific, the "background" due to circulating radioactivity is greatly reduced. Furthermore, imaging by intracoronary injection is almost instantaneous since the imaging agent reaches the site of the thrombus immediately.

BRIEF DESCRIPTION OF THE DRAWINGS

FIG. 13 illustrates the changes in thrombus coronary radioactivity during streptokinase-induced thrombolysis.

DETAILED DESCRIPTION OF THE INVENTION

Figure 1:
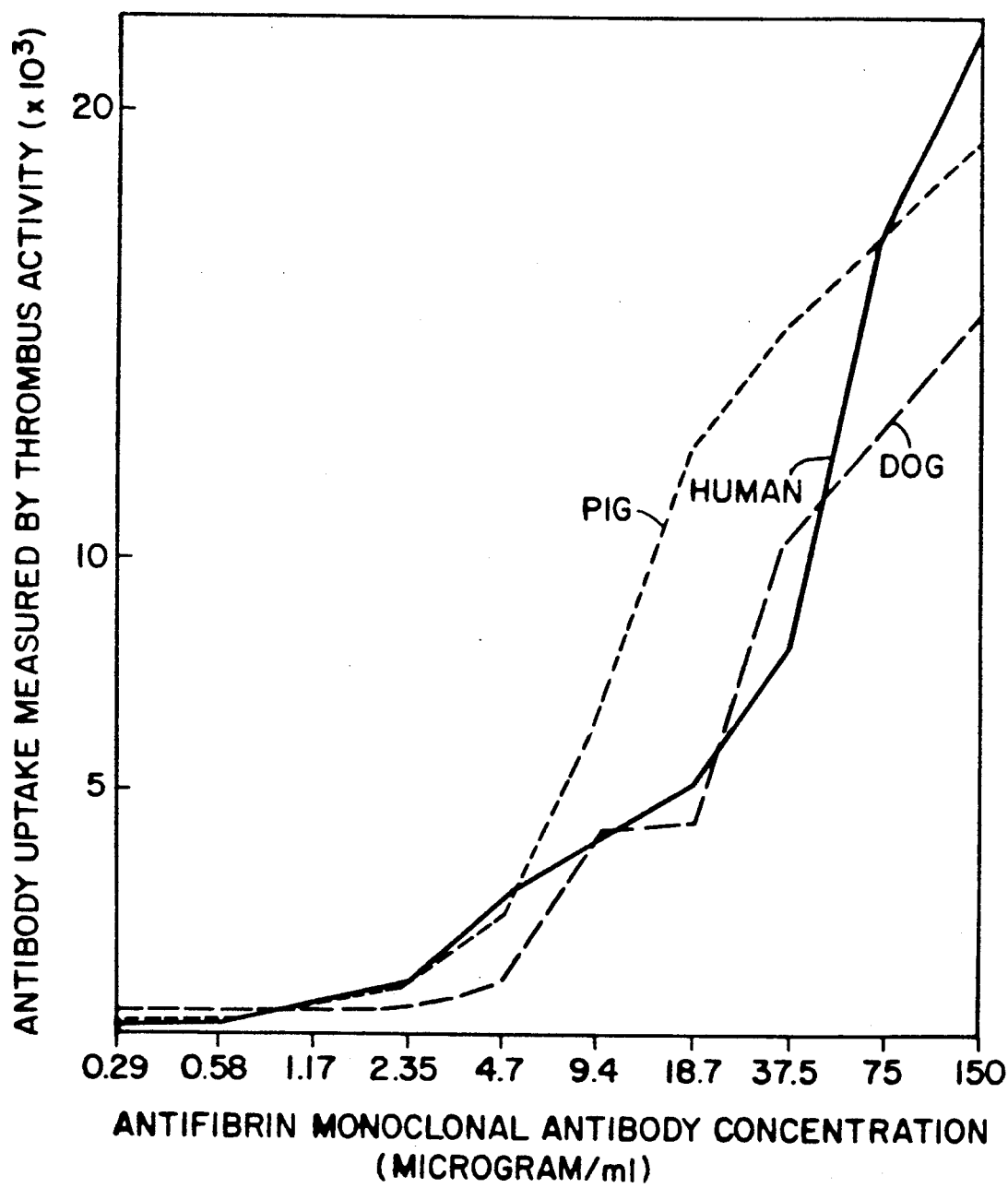
FIG. 1 graphically represents the direct relationship between increasing concentration of radiolabeled monoclonal antibody and uptake by a thrombus in a dog.

Methods of this invention for rapid imaging of coronary thrombi comprise administration of radio-labeled monoclonal antibodies (or fragments) against thrombi-specific components directly into a coronary artery. This provides for instantaneous imaging of coronary thrombi.

The preferred thrombin-specific antibodies for the methods of the invention are specific for fibrin. Particularly preferred are anti-fibrin monoclonal antibodies such as T2G1, developed against the NH$_2$-terminus of the beta-chain of fibrin II. Kudryk, B. et al., *Mol. Immunol.*, 21:89 (1984). Also useful is the fibrin specific monoclonal antibody 59D8 generated by using hemocyaninconjugates of a synthetic peptide. Antibodies 59D8 and T2G1 are comparable since they apparently bind to the same epitope.

Another fibrin-specific antibody useful in methods of this invention is the antibody GC4 (IgG1, Kappa) which reacts with digest products of fibrin. The antibody does not bind to ELISA plates coated with fibrinogen, fibrin monomer, or any of the three component chains of fibrinogen. It appears to be directed to a conformation-dependent epitope associated with one or more chains of the distal domain of fibrinogen or fibrin. It may, therefore, bind to partially degraded thrombi.

An immunoscintigraphic image of a coronary thrombus can also be obtained with radiolabeled antibodies specific for activated platelets. Preferred platelet-specific antibodies for coronary imaging are specific for an epitope of the GMP-140 protein, a marker of activated platelets. Stenberg et al., *J. Cell. Biol.* A particularly preferred anti-platelet antibody useful for imaging coronary thrombi is monoclonal antibody S12. McEver, R.P. and M.N. Martin, *J. Biol. Chem.*, 259:9799 (1984).

Other monoclonal immunoglobulins of this invention specific for fibrin and/or platelets can be obtained from lymphoid cells which produce the antibodies against the desired antigen.

In the method of this invention, antibody fragments, rather than whole antibody molecules, are generally preferred. Because they are directly injected intravascularly antibody fragments accumulate at the thrombus more rapidly. Thus an image can be obtained in less time than is possible using subcutaneous injections. These fragments are also cleared more rapidly from tissues, resulting in a lower background signal. See, e.g., Haber et al., U.S. Pat. No. 4,036,945; Goldenberg et al., U.S. Pat. No. 4,331,647. The antigen binding fragments Fab' and F(ab')$_2$ are preferred. The F(ab')$_2$ fragment can be prepared by digestion of the whole immunoglobulin molecule with pepsin according to any of several well known protocols. The Fab' fragment can be prepared by chemical reduction of F(ab')$_2$ fragments. In its most preferred configuration, T2G1 is administered as an Fab' fragment. In addition, fragments can also be prepared by recombinant DNA techniques. See, for example, U.S. patent application Ser. No. 195,720 (Coller and Knight), filed May 18, 1988, the teachings of which are incorporated by reference herein.

The antibodies or antibody fragments can be labelled with radioisotopes which are suitable for detection by external scintigraphy. The gammaemitters Indium-111 and Technetium-99m are preferred because these radiometals are detectable with a gamma camera and have favorable half-lives in vivo. Technetium-99m is an ideal radionuclide for scintigraphic imaging because of its nuclear properties. It has a single photon energy of 140 KeV, a half-life of about 6 hours, and it is readily available from a $^{99}$Mo-$^{99m}$Tc generator.

Antibodies can be labelled by any of the many techniques known in the art. The preferred technique for technetium-99m labelling is that of Pak, K.Y et al., U.S. patent application Ser. No. 034,003, filed Apr. 2, 1987, the teachings of which are incorporated herein. Antibody can also be labeled via a chelating agent such as diethylenetriaminepentaacetic acid (DTPA) which is conjugated to the antibody. In this indirect labelling approach, the radiometal is chelated by the chelating agent attached to the antibody See, for example, Khaw et al., *Science*, 209:295-297 (1980) Krejcarek et al., *Biochem. Biophys. Res. Commun.*, 77:581-585 (1977); Childs, R.L. and Hnatowich, D.J., *J. Nucl. Med.*, 26:293 (1985).

A simple method for labeling anti-fibrin monoclonal antibody (T2G1) with Technitium-99m is as follows:

1. Remove a predetermined amount (i.e., 0.5 mg) of T2G1 from a vial and add it to a second vial containing citrate buffer. Invert vial several times to mix.

2. Place vial in lead shield. Add freshly eluted sodium pertechnetate containing a predetermined level of isotopic activity (e.g., 15 mCi) to vial.

3. Invert vial several times to mix contents. Incubate at room temperature.

4. Draw the radiolabeled dose into a shielded syringe through a low protein-binding 0.2-0.22 micron filter.

5. Radiolabeled antibody may be diluted with 0.9% saline for injection if desired.

The monoclonal antibodies or antibody fragments used in the method of this invention are administered to a patient suspected of having coronary thrombi in the form of injectable compositions. In preferred methods of this invention, labeled antibody solution is injected directly into the coronary artery. Direct intracoronary injection allows for essentially instantaneous accumulation of labeled monoclonal antibody at the thrombus site. A typical injectable composition of imaging agent may contain human serum albumin, and a quantity of radiolabeled specific antibody in neutral phosphate buffer containing physiological saline.

After sufficient time to allow the labeled immunoglobulin to localize, the signal generated by the label is detected by a photoscanning device such as a gamma camera.

A preferred method of rapid imaging of coronary thrombi comprises the steps of:

a. administering via direct intracoronary injection an anti-fibrin monoclonal antibody such as T2G1 or Fab' fragment of T2G1 labeled with Technetium-99m (Tc-99m);

b. allowing the Tc-99m labeled antibody to accumulate at the thrombus site;

c. detecting the gamma radiation signal with a gamma camera; and d. converting the signal generated by the labeled antibody into a visual image of the coronary thrombus.

Methods of this invention can also be used to monitor thrombolysis in a patient with a coronary thrombus. For example this can be done in connection with thrombolytic therapy using, for example, tissue plasminogen activator or streptokinase. In this embodiment, labeled thrombus-specific monoclonal antibody is administered to the patient via the coronary artery and the signal generated by the radiolabel is detected and scanned over a predetermined time period. The signal can be converted into a series of visual images over an appropriate time period. In this way, a sequence of images is generated that reveals the extent and time course of thrombolysis.

The methods of this invention have several significant advantages.

1) since the imaging agent is thrombus-specific, the "background" due to circulating radioactivity is eliminated;

2) the method is less dependent on the age of the thrombus than the In-111 platelet method; it is useful when thrombi have stabilized or are dissolving, in addition to being useful when thrombi are propagating; and 3) instant imaging by intracoronary injection is feasible since very little time is needed for incorporation of the labeled antibody into the thrombus.

This invention is illustrated further by the following examples.

EXAMPLE 1

Cross-reactivity of murine anti-human fibrin monoclonal antibody

This Example illustrates that in vitro thrombus uptake of murine anti-human fibrin increases with increasing antibody dose. Ten different dilutions of technetium-99m labeled T2G1 monoclonal antibody (Tc-99m MAb) are prepared in 10 beakers using serum dilution technique, resulting in a range of concentration from 0.29 to 150 ug/ml. For each antibody experiment, thirty capillary tubes are divided into 3 sets of 10 and each set is filled with either human, canine, or swine blood. Since the T2G1 MAb is directed to an epitope located on a region of the beta chain which can rapidly be cleaved by plasmin digestion, in vitro clotting can be carried out in the presence of 100 KIU Trasylol/ml. The capillary tubes are incubated for 2 hours. Equal size clots from the 3 species are then placed inside beakers containing various concentration of Tc-99m T2G1 and incubated in a water bath at 37° for 2 hours. FIG. 1 shows that: 1) with increasing concentration of Tc-99m T2G1 MAb, thrombus radioactivity increases and 2) there does not appear to be a significant difference between the 3 species with respect to thrombus-antibody binding. These preliminary data suggest that murine anti-human fibrin MAb crossreacts with canine and swine fibrin in vitro and suggest that swine and canine models may be used for thrombus imaging experiments with technetium labeled T2G1 MAb. Furthermore, it appears that in vitro thrombus uptake of MAb increases with increasing MAb dose.

EXAMPLE 2

Uptake of Tc-99m labeled monoclonal antibody

This Example illustrates that, for normal size thrombi, brief exposure to antibody results in adequate uptake.

Figure 2:
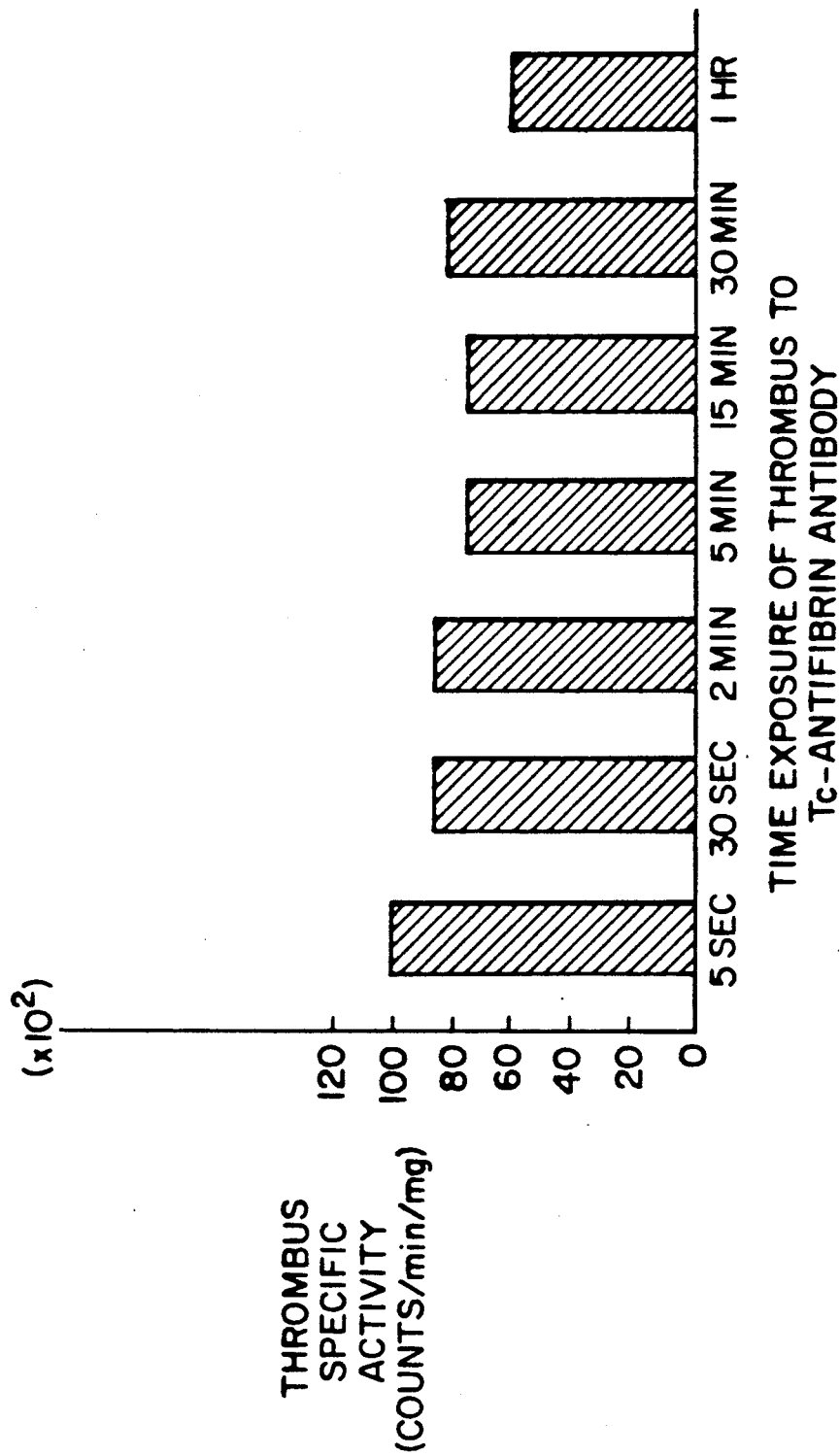
FIG. 2 shows the relationship between in vitro uptake of radiolabeled monoclonal antibody T2G1 and time of exposure to antibody in a human thrombi of small size.
Figure 3:
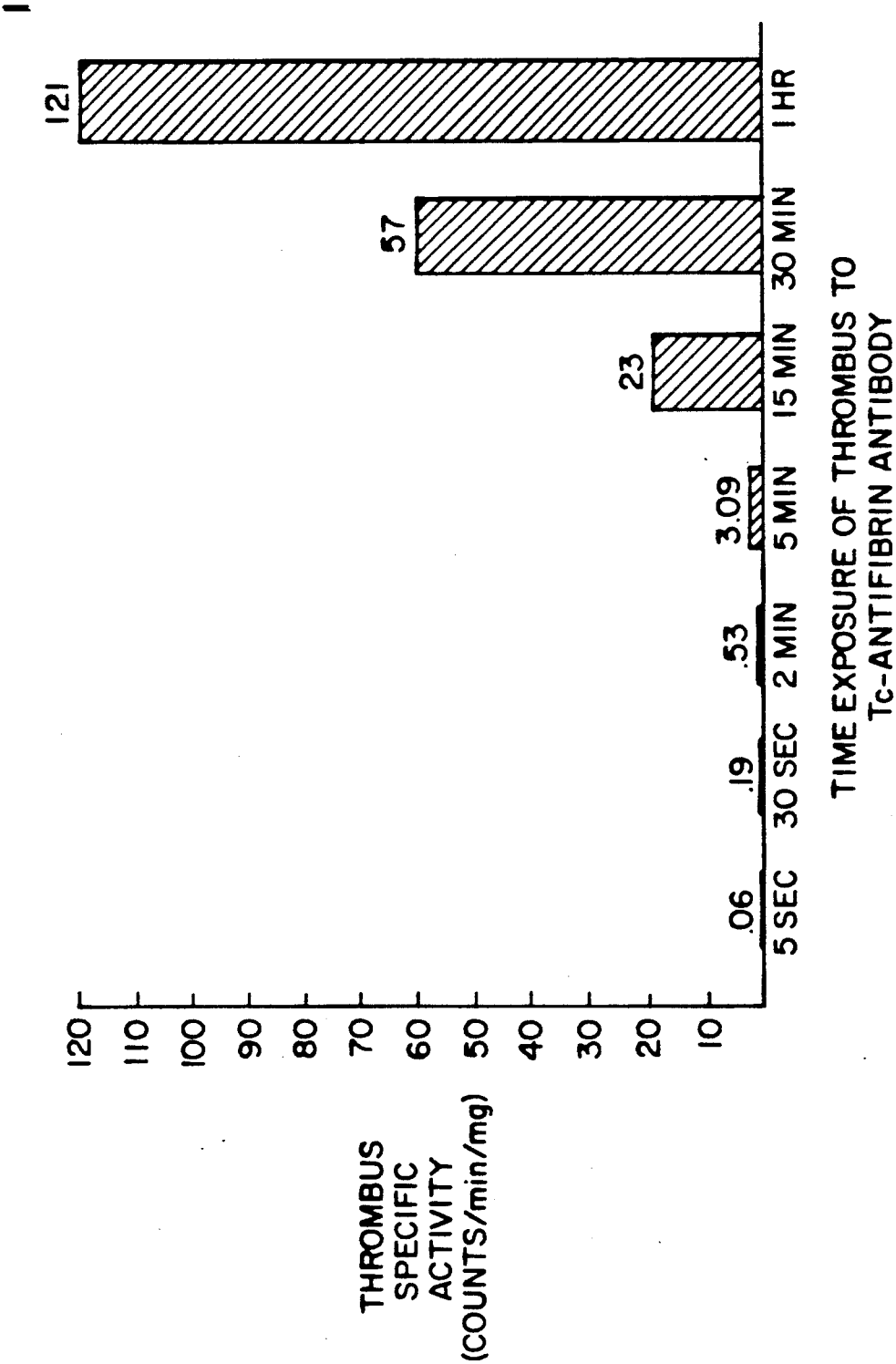
FIG. 3 shows the effect of time of exposure to labeled antibody on in vitro uptake of antibody for a human thrombi of large size.

Seven equal size human thrombi are prepared by clotting human blood (2 hours/37° C.) with thrombin, in the presence of 5 mM of calcium chloride. The weight of thrombi range from 32 to 42 mg. In a second experiment, seven additional equal size human thrombi are prepared in a similar manner but their sizes range from 1010 to 1130 mg. Each washed clot is then placed in the same concentration of Tc-T2G1 MAb (0.25 mg/ml of MAb labeled with 5 mCi of Tc-99m pertechnetate). Clots are left in the MAb solutions for 5 and 30 seconds as well as 2, 4, 15, 30 and 60 minutes. Following exposure, the clots are washed thoroughly and counted in the scintillation well counter. FIG. 2 demonstrates that with small thrombi (approximately 35 mg) in vitro MAb uptake occurs within 5 seconds of exposure and that thrombus uptake does not further increase at longer exposure times. FIG. 3 shows that with relatively larger thrombi (approximately 1,000 mg) increasing exposure time results in greater MAb uptake by the thrombus. These results suggest that with a relatively small thrombus, in the size range normally encountered in the intracoronary system, brief exposure results in adequate Tc-T2G1 MAb uptake.

EXAMPLE 3

In vivo thrombus imaging of very small occlusive clots

Animal preparation: Mongrel dogs of 25-35 kg are studied. Approximately 0.5 to 1.0 mg/kg of acepromazine is first administered intramuscularly. In half an hour 10 mg/kg of thiamolol is administered intravenously for anesthesia. This is followed by an Enflurane 102 mixture throughout the experiment through the FT tube used for maintenance of anesthesia. The animals are intubated and artificially ventilated with room air. A continuous IV drip of Lidocaine (1 mg/min) is given in the coronary thrombus experiments when ventricular arrythmia develops. Intravenous access is established via femoral vein. Systemic blood pressure and surface electrocardiogram are monitored throughout the experiment.

Thrombus induction by copper coil technique: For carotid artery experiments, the artery is dissected, exposed and ligated distally. A small incision is made in the arterial wall. A previously weighed and measured copper coil is inserted through this small incision. After the coil is in place, a second ligation is performed proximal to the incision site. For femoral artery experiments, a guide wire is advanced from one of the carotid arteries to the femoral artery. A copper coil is then threaded over a guide wire and pushed along the guide wire into position by an angiography catheter. For coronary artery experiments a copper coil is threaded over a guide wire and pushed along into one of the coronary arteries using a coronary catheter. After 60 minutes waiting period following placement of copper coil in the desired location, presence of the thrombus is verified by contrast fluoroscopy.

Thrombus induction without a copper coil: This technique is utilized to induce thrombi in peripheral arteries. The artery is dissected and exposed. Two clamps are placed one centimeter apart so that the section of the artery in between the two clamps will contain blood. Thrombin is injected (dose: 5 NIH units) inside the clamped portion to induce thrombus formation. The artery is then ligated at the site of the distal clamp and the proximal clamp is then removed. The animal is then heparinized (dose: 200 U/kg).

In vivo imaging

Figure 4:
FIG. 4 shows in vivo images of a small coronary thrombus of a dog after intracoronary injection of Tc-99m T2G1 monoclonal antibody.
Figure 4:
Figure 4:
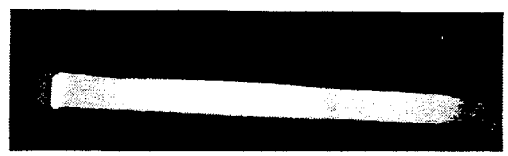

A copper coil (10 mm long with a diameter of 2 mm) is inserted in the diagonal coronary artery to induce intracoronary thrombus in a closed chest dog model. After confirming the presence of coronary thrombus by contrast angiography, the dog is heparinized. Subsequently, 1.2 mCi of Tc-99m antifibrin antibody is injected intracoronarily a few millimeters away from the clot through an infusing catheter. FIG. 4 demonstrates the in vivo image of the intracoronary clot 3 minutes after Tc-T2G1 MAb injection. As shown blood radioactivity was minimal. After sacrifice, localization of radioactivity in the coronary clot was confirmed by ex vivo imaging of the thrombus and the vessel wall (FIG. 4). The clot is then divided into three sections which are separately weighed and counted in a well counter. In this particular example, the proximal portion of the clot weighed 5 mgs and showed maximum activity ($1.2 \times 10^6$ cpm). As a reference, a clot with a volume of 1 mm$^3$ weighs approximately one mg. This proximal portion represented the part of the clot which was rapidly visualized in vivo. The ex vivo activity of the proximal clot was significantly higher than the mid and distal portions ($0.6 \times 10^5$ and $1.6 \times 10^5$ cpm respectively). These data suggest that a 5 mg totally occlusive intracoronary clot can be rapidly visualized by intracoronary administration of a small dose of Tc-99m antifibrin MAb. This experiment also suggests that with intracoronary injection of the radiolabeled MAb, blood pool activity is negligible and high target to background ratios can be obtained. It appears that the proximal portion of a totally occlusive clot (the portion exposed to the labeled MAb) exhibits maximum radioactivity.

EXAMPLE 4

Thrombus imaging of small, partially blocked thrombi

Figure 5:
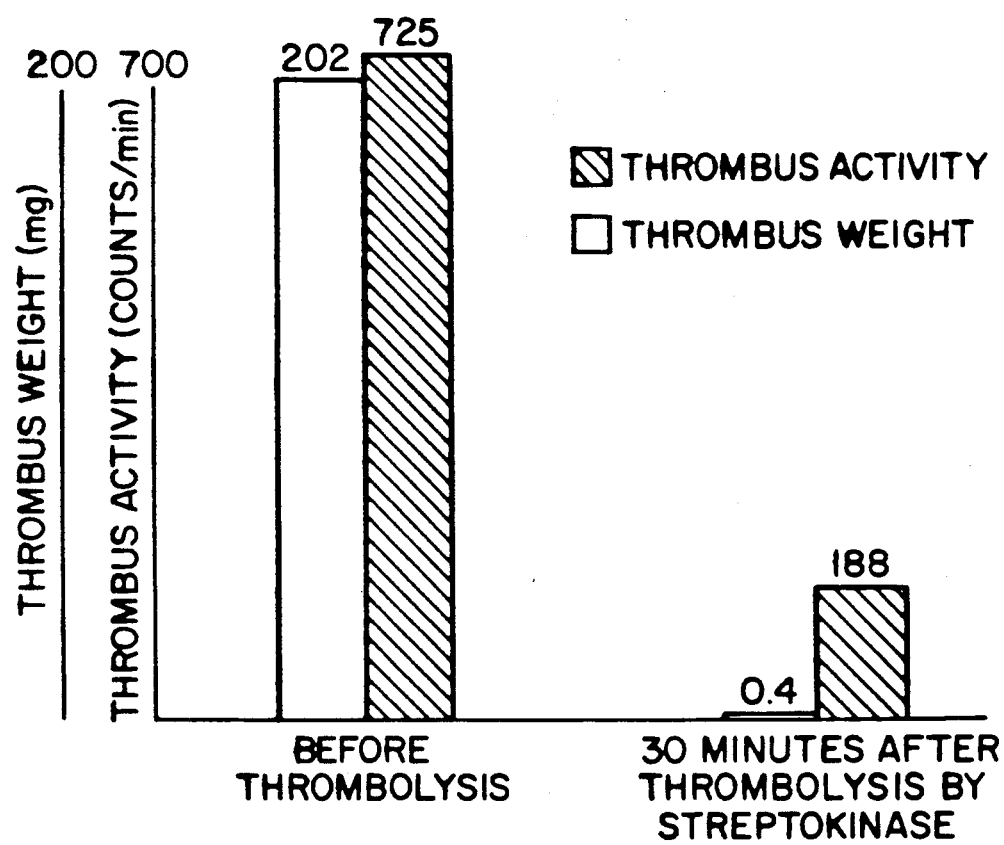
FIG. 5 shows detection of a small, partially blocked carotid artery thrombus of a dog using Tc-99m T2G1.
Figure 6:
FIG. 6 shows an in vivo image of a small partially occluded carotid thrombus of a dog after intraarterial injection of Tc-99m monoclonal antibody T2G1.
Figure 6:

For intra-arterial experiments, a venus thrombus is formed by inserting a copper coil in the jugular vein of a mongrel dog. After one hour, the venous clot is harvested. The coil containing the washed thrombus is submerged for 2 minutes in a solution of Tc-T2G1 MAb (0.5 mg of MAb labeled to 4 mCi of Tc-99m). The coil is then transplanted into the carotid artery. After a baseline scintigram, 750,000 units of streptokinase is infused intravenously. After 30 minutes, in the example shown in FIGS. 5 and 6, thrombus radioactivity was diminished but was still present. The animal is then sacrificed and the carotid artery clot is excised, weighed and imaged again under the camera ex vivo. The thrombus weighed only 0.4 mg (FIG. 5) and ex vivo images demonstrated activity to be localized in the thrombus but not in the surrounding structures (FIG. 6). This preliminary study demonstrates that a 0.4 mg partially occlusive intraarterial thrombus can be imaged in vivo by Tc-99m T2G1 MAb.

Figure 7:
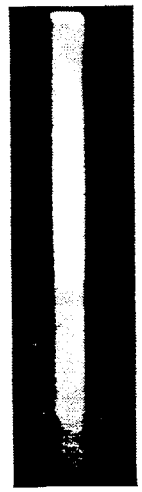
FIG. 7 shows an image of a partially occluded coronary arterial thrombus of a dog using intracoronary injection of Tc-99m monoclonal antibody T2G1.
Figure 7:
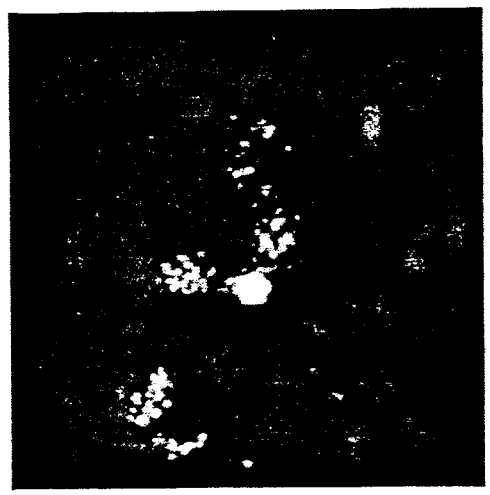

For experiments involving partially occluded intracoronary thrombi, a copper coil was inserted inside the marginal branch of the circumflex coronary artery of a closed chest dog. Formation of thrombus was confirmed by contrast angiography. During the ensuing 60 minutes, a total of 250,000 units of streptokinase was infused intracornarily and patency of the coronary artery was assessed by multiple contrast arteriograms. At the end of 1 hour, partial reperfusion was noted. Exactly 2.5 mCi of Tc-T2G1 MAb was infused into the coronary artery. Intense radioactivity was noted in the region of coil insertion (FIG. 7). Immediately after imaging, the animal was sacrificed, and the presence of residual partially occlusive thrombus in the copper coil was confirmed by direct examination of the coil. The partially occlusive thrombus weighed 0.5 mg. This preliminary finding suggests that small residual intracoronary clot may be detected rapidly by intracoronary administration of Tc-antifibrin MAb.

EXAMPLE 5

Detection of peripheral human venous thrombi

Figure 8:
FIG. 8 shows an in vivo detection in a human patient of a venous thrombus using direct intravenous injection of Tc-99m monoclonal antibody T2G1.
Figure 8:
Figure 8:
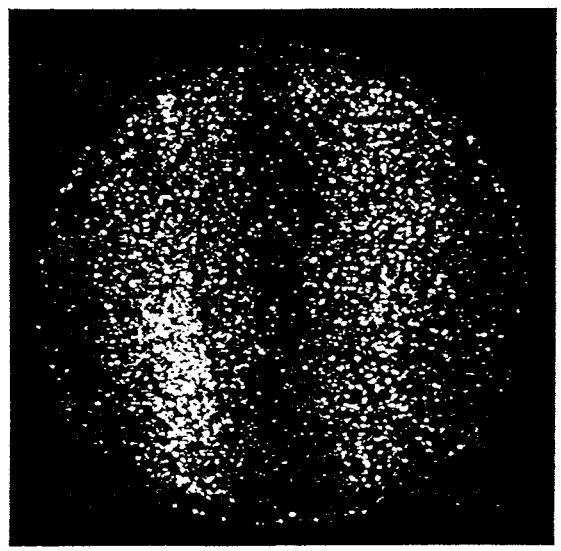
Figure 9:
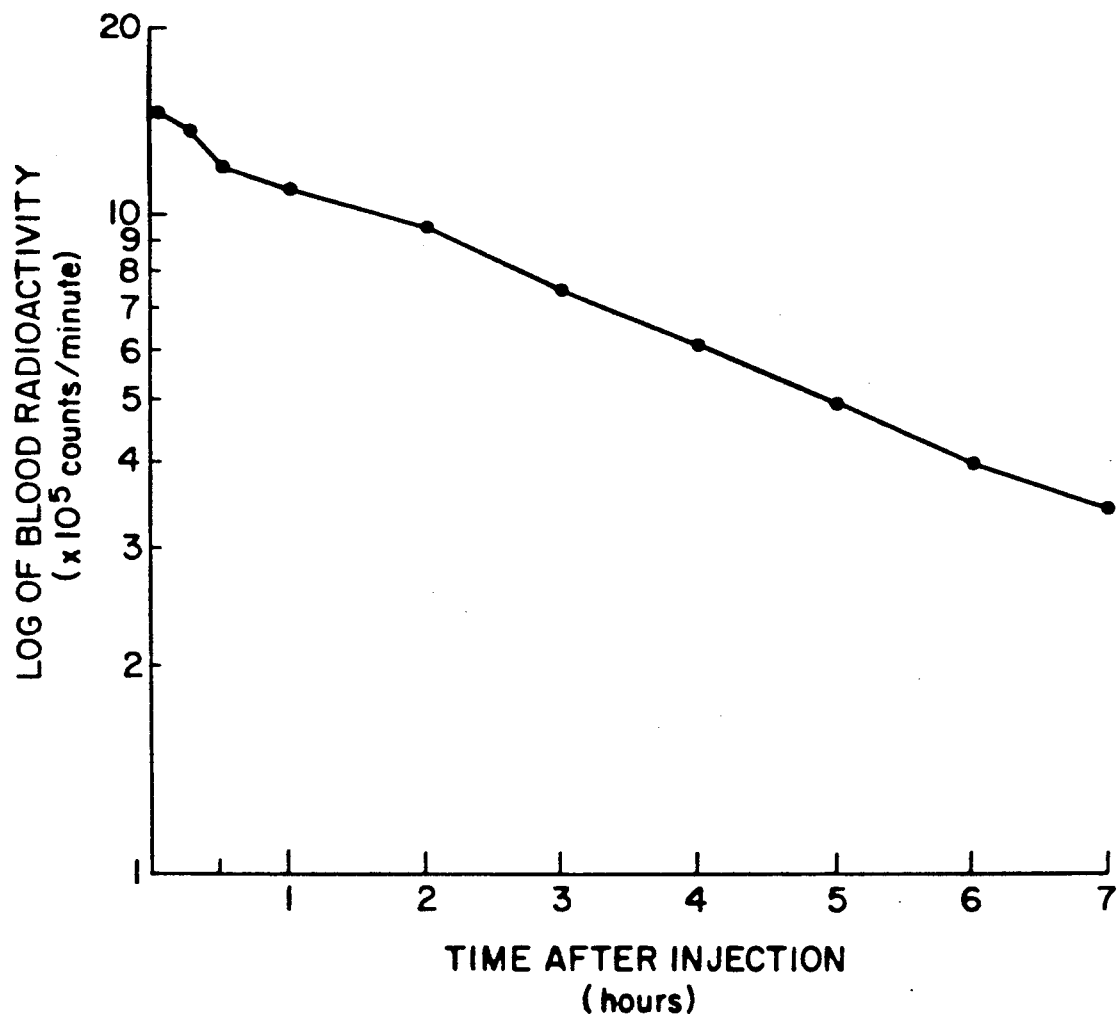
FIG. 9 illustrates the disappearance of Tc-99m monoclonal antibody T2G1 from the blood of a human patient after administration.

This Example illustrates that in vivo imaging of human peripheral arterial thrombus may be feasible by intravenous injection of radiolabeled MAb's. After informed consent was obtained, a dose of 15 mCi (0.5 mg MAb) of Tc-T2G1 MAb has been injected intravenously in a patient suspected of having deep venous thrombosis. Planar images were obtained of both calves (posterior tibia views) at 5 minutes, 4 hours and 24 hours after injection. FIG. 8 shows increased radioactivity in the left tibial area as early as 4 hours following injection of Tc-T2G1 MAb. Blood disappearance of Tc-T2G1 MAb was rather fast with a T ½ of 180 minutes (FIG. 9). This observation demonstrates that a peripheral venous thrombus can be imaged by intravenous administration of Tc-T2G1 MAb with adequate target to background ratio.

EXAMPLE 6

Effect of monoclonal antibody methods on thrombolysis

This series of experiments illustrates the important point that treatment of in vivo and in vitro thrombi with anti-fibrin (MAb) has little effect on subsequent breakdown of the thrombus.

1. Baseline rate of change in radioactivity of the thrombus over time without extrinsic thrombolysis. In a closed chest dog, intracoronary thrombus was induced by insertion of a copper coil inside the diagonal coronary artery. Prior to, and following intracoronary injection of 1.5 mCi of Technetium-99m-T2G1 MAb, serial 2 minute images were obtained over the region of the heart for 150 minutes. Radioactivity vs. time curves in the region of the thrombus reveal that radioactivity tends to decrease exponentially over time with a T ½ of 120 minutes. These results show that following attachment of Tc-99m T2G1 MAb to thrombus, there is gradual loss of radioactivity presumably due to intrinsic thrombolysis.

Figure 10:
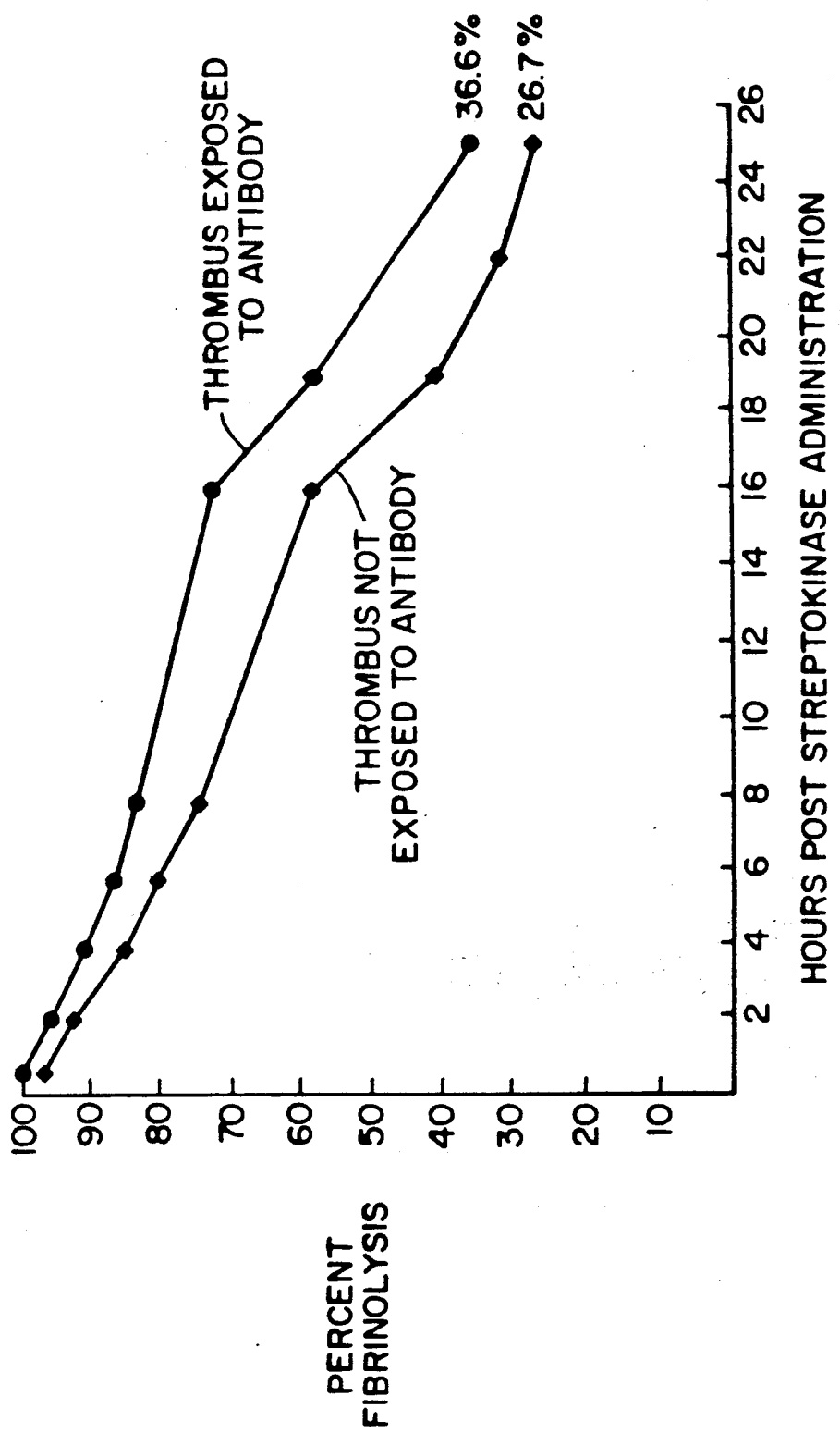
FIG. 10 illustrates the effect of monoclonal antibody T2G1 administration on subsequent streptokinase-induced thrombolysis.
Figure 11:
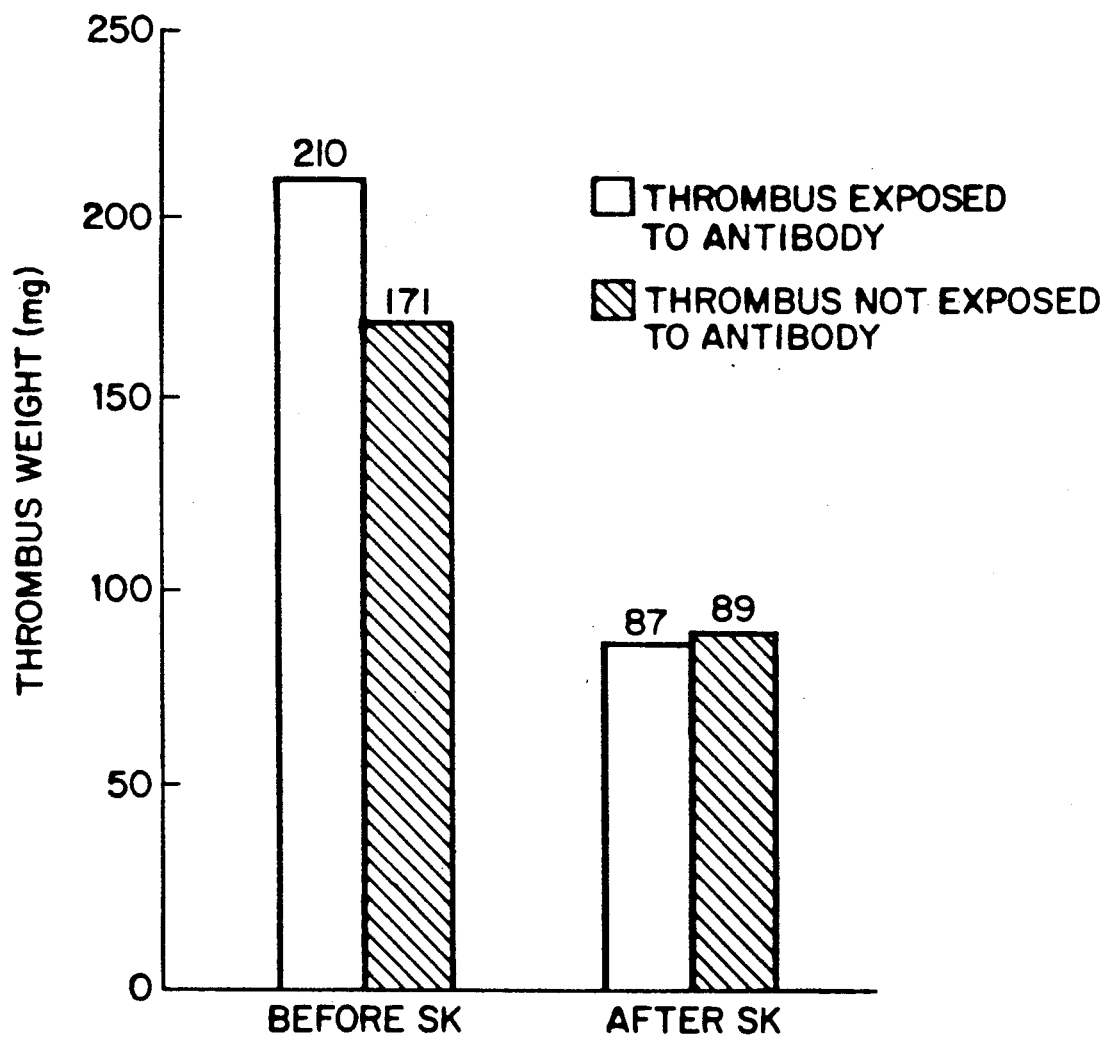
FIG. 11 shows the change in thrombus weight after thrombolysis with and without pretreatment with monoclonal antibody T2G1.

2. Injection of radiolabeled imaging antibodies does not adversely affect thrombolysis. a) In vitro experiments: Fifteen ml of citrated human blood has been mixed with 20 mM of calcium chloride (200 ul) and 10 mCi of Iodine (I)-125 labeled fibrinogen (in 2 ml of normal saline). Twenty NIH units of thrombin is added to the blood which is then incubated in water bath at 37° for 2 hours. At the end of incubation, a thrombus is formed which has incorporated I-125 fibrinogen. The thrombus is cut into 2 sections weighing 984 mg and 1112 mg which are then put in 2 separate tubes. The thrombus in the first tube is incubated with 0.25 mg of MAb (in 2.5 ml) for 30 minutes. In both tubes, 125,000 units of streptokinase (in 1 ml) and 10 units of heparin (in 1 ml) are added. Both tubes are then incubated in water bath at 37°. At several time intervals, 2 ml of the supernatant is counted in the well counter for I-125 activity which reflects the amount of released I-125 from the thrombus due to fibrinolysis. FIG. 10 compares the rate of lysis of the thrombus already incubated in antifibrin MAb and the control thrombus not exposed to the MAb. The rate of thrombolysis and ultimate % lysis appears to be similar regardless of pre-treatment with antifibrin MAb. In this in vitro experiment the dose of MAb was five times greater than the dosage during in vivo imaging. These data suggest that use of MAb for imaging does not prevent subsequent lysis of the labeled clot by streptokinase.

b) In vivo experiments: In a mongrel dog, equal size copper coils have been inserted inside the left and right jugular veins and left in place for 1 hour for thrombus formation. Thrombi are then harvested. One of the thrombi weighing 210 mg is placed in a solution containing 0.5 mg of T2G1 MAb and then implanted into the right femoral artery. The second thrombus, weighing 171 mg, is placed in normal saline and then inserted into the left femoral artery to serve as a control. Four thousand units of heparin is then given to prevent further propagation of thrombi. A baseline contrast angiogram is obtained with the catheter at the bifurcation of the iliac artery demonstrating complete occlusion of both femoral arteries due to transplanted thrombi. One million units of streptokinase is then administered intravenously. Sixty minutes after streptokinase administration, selective catheterization of the two femoral arteries revealed patency. The transplanted copper coils were immediately retrieved and weighed. In comparing the thrombi with and without pre-treatment with antifibrin T2G1 MAb results demonstrated that thrombi weighed approximately the same FIG. 11). This result confirms the in vitro data that pre-treatment of in vivo thrombus with antifibrin (T2G1) MAb does not adversely effect thrombolysis.

Figure 12:
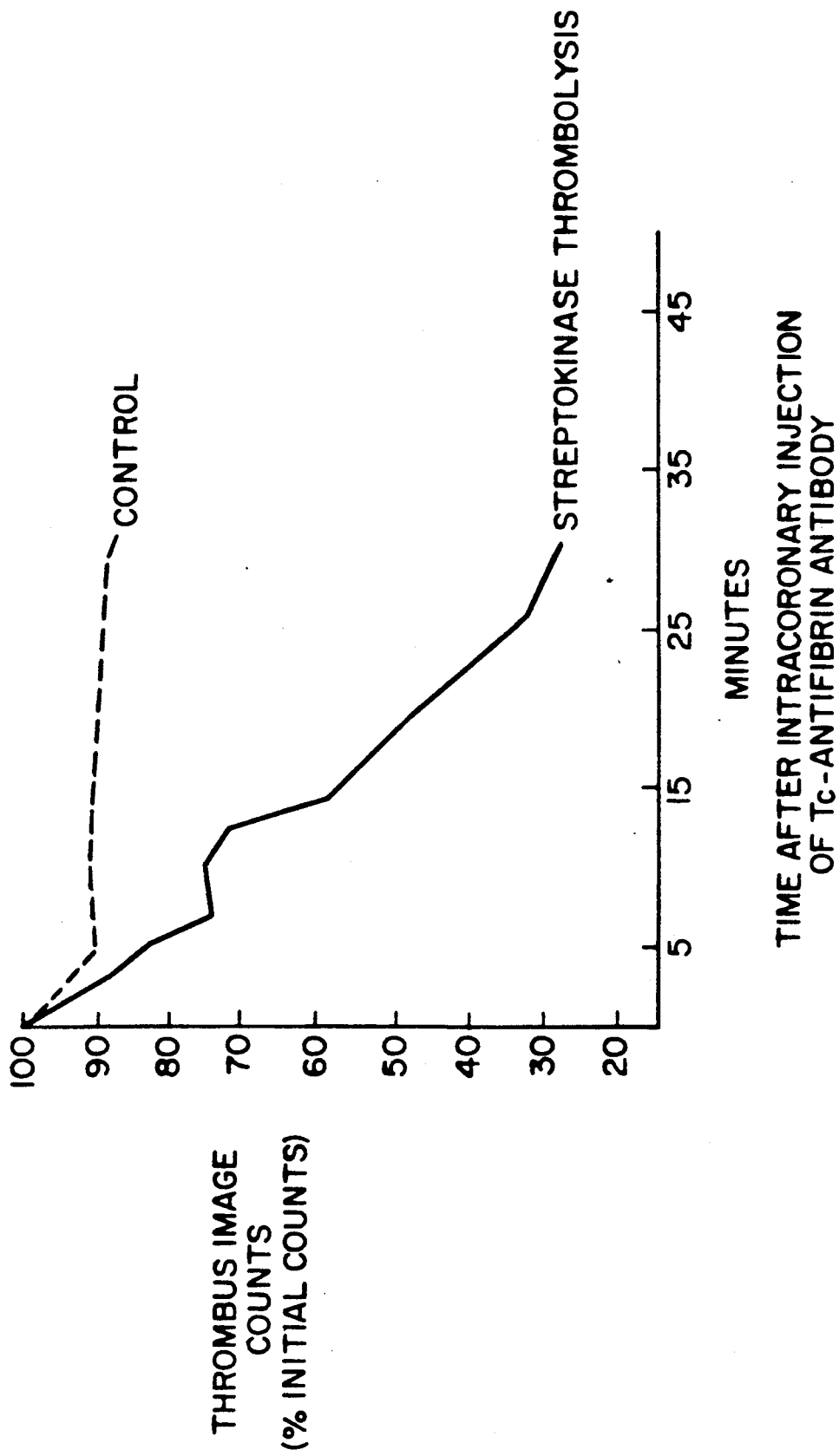
FIG. 12 shows the change in Tc-99m-radioactivity during thrombolysis as compared to a thrombus not undergoing thrombolysis.

3. Thrombolysis monitored noninvasively by radiolabeled MAb imaging. a) Peripheral artery thrombus experiment: In a mongrel dog, a venous thrombus is formed one hour after insertion of a copper coil into the jugular vein. The thrombus is harvested and exposed to 2 mCi of Tc-99m-T2G1 MAb and reinserted into the carotid artery. One million units of streptokinase is then administered intravenously. Multiple, two minute static images are obtained over the carotid region for a total of 30 minutes. Regions of interest are assigned to the thrombus images to determine change of thrombus radioactivity over time. FIG. 12 demonstrates a steady decline of thrombus radioactivity during thrombolysis. For comparison, the control curve is also shown. Rate of decline of thrombus radioactivity during thrombolysis is significantly faster than the control.

b) Coronary artery thrombus experiment: In a dog, intracoronary thrombus was induced in the marginal branch of the left circumflex coronary artery. Exactly 2.5 mCi of Tc-99m antifibrin MAb was infused intracoronarily and the thrombus was visualized instantaneously. Serial 2 minute static images were obtained for 60 minutes without treatment. The 250,000 units of streptokinase (STK) was infused over 60 minutes intracoronarily. Again, serial images were taken for 60 minutes. FIG. 13 demonstrates changes in thrombus radioactivity during the control observation period (23 A-C) and after intracoronary administration of streptokinase (23 D-F). Prior to administration of intracoronary streptokinase, thrombus radioactivity declined slightly over a period of 24 minutes. With intracoronary administration of streptokinase, thrombus radioactivity and size diminished rapidly. These results suggest that coronary thrombolysis can be noninvasively monitored by measuring changes in thrombus radioactivity.

Equivalents

Those skilled in the art will recognize or be able to ascertain, using no more than routine experimentation, many equivalents to the specific embodiments of the invention described herein. Such equivalents are intended to be encompassed in the following claims.

We claim:
1. A method of imaging a coronary thrombus in a patient, comprising the steps of:
   a. administering directly into a cornary artery of a patient suspected of having an coronary thrombus a radiolabeled monoclonal antibody or antibody fragment specific for a thrombus component;
   b. allowing the radiolabeled monoclonal antibody or antibody fragment to accumulate at the thrombus site;
   c. detecting the signal generated by the radiolabel with a photoscanning device;
   d. converting the signal generated into a visual image of the thrombus.
2. A method of claim 1, wherein the monoclonal antibody or antibody fragment is specific for fibrin.
3. A method of claim 1, wherein the monoclonal antibody or antibody fragment is specific for platelets.
4. A method of claim 2, wherein the anti-fibrin monoclonal antibody or antibody fragment is labeled with Technetium-99m or Indium-111.
5. A method of claim 4, wherein the antibody fragment is the Fab', F(ab')$_2$ or F$_v$ fragment.
6. A method of imaging coronary thrombi in a patient suspected of having a coronary blood clot, comprising the steps of:
   a. administering to the patient via direct intracoronary artery injection, a Technetium-99m-radiolabeled anti-fibrin antibody fragment;
   b. allowing the radiolabeled reactive antifibrin fragment to accumulate at the thrombus;
   c. detecting the signal generated by a gamma camera;
   d. converting the signal generated into a visual image of the plaque.
7. A method of claim 6, wherein the radiolabeled antifibrin monoclonal antibody is selected from the group consisting of GC4, T2G1 and antibody fragments of T2G1 and GC4.
8. A method of claim 7, wherein the antibody fragment is selected from the group consisting of Fab', F(ab')$_2$ and F(v) fragments.
9. A method of monitoring thrombolysis in a patient having a coronary thrombus, comprising the steps of:
   a. administering to the patient via direct intracoronary artery injection, a Technetium-99m-radiolabeled anti-fibrin Fab antibody fragment;
   b. allowing the radiolabeled reactive antifibrin fragment to accumulate at the thrombus;
   c. detecting the signal generated at periodic intervals over time using a photoscanning device; and
   d. converting the signal generated into a time-series of images of the thrombus to determine the extent and course of thrombolysis.
10. A method of claim 9, wherein the radiolabeled antifibrin monoclonal antibody is selected from the group consisting of GC4, T2G1 and antibody fragments of T2G1 and GC4.
11. A method of claim 10, wherein the antibody fragment is selected from the group consisting of Fab', F(ab')$_2$ and F(v) fragments.
12. A method of claim 9, wherein the thrombus imaging is done in conjuction with thrombolytic therapy.

* * * * *